United States Patent [19]
Malmgren

[11] Patent Number: 5,513,793
[45] Date of Patent: May 7, 1996

[54] BRAZELESS CERAMIC-TO-METAL BOND FOR USE IN IMPLANTABLE DEVICES

[75] Inventor: Richard P. Malmgren, Castaic, Calif.

[73] Assignee: Advanced Bionics Corporation, Sylmar, Calif.

[21] Appl. No.: 319,580

[22] Filed: Oct. 7, 1994

[51] Int. Cl.⁶ .................................. B23K 20/00
[52] U.S. Cl. .................. 228/193; 228/212; 228/262.21
[58] Field of Search .................................. 228/190, 193, 228/195, 124.6, 212, 262.21, 262.71

[56] References Cited

U.S. PATENT DOCUMENTS

| Re. 33,859 | 3/1992 | Gurol | 428/76 |
|---|---|---|---|
| 4,041,955 | 8/1977 | Kelly et al. | 128/419 P |
| 4,159,075 | 6/1979 | Ljung et al. | 228/116 |
| 4,525,766 | 6/1985 | Petersen | 361/283 |
| 4,618,802 | 10/1986 | Schrank | 313/512 |
| 4,627,958 | 12/1986 | Hays | 419/8 |
| 4,693,409 | 9/1987 | Mizunoya et al. | 228/262.21 |
| 4,725,480 | 2/1988 | Gurol | 428/210 |
| 4,729,504 | 3/1988 | Edamura | 228/262.72 |
| 4,861,641 | 8/1989 | Foster et al. | 428/137 |
| 4,882,298 | 11/1989 | Moeller et al. | 437/212 |
| 4,906,311 | 3/1990 | Gurol | 156/89 |
| 4,991,582 | 2/1991 | Byers et al. | 128/419 P |
| 5,181,647 | 1/1993 | Runyan | 228/44.3 |

FOREIGN PATENT DOCUMENTS 9408539  4/1994  WIPO .

Primary Examiner—Samuel M. Heinrich
Attorney, Agent, or Firm—Fitch, Even, Tabin & Flannery

[57] ABSTRACT

In a method and apparatus for forming a hermetically sealed bond for use in implantable medical devices, a first structure, made from a first material, is positioned against a second structure, made from a second material. A compressive force directed at the second structure is applied to the first structure, and an equal force directed at the first structure in a direction opposite the compressive force is applied to the second structure so that the first and second structures are isodynamically pressed together. The first and second structures are heated to a diffusion temperature whereat the first material and the second material undergo diffusion, thereby forming a hermetically sealed bond between the first and second materials.

15 Claims, 2 Drawing Sheets

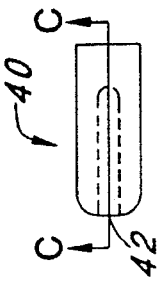
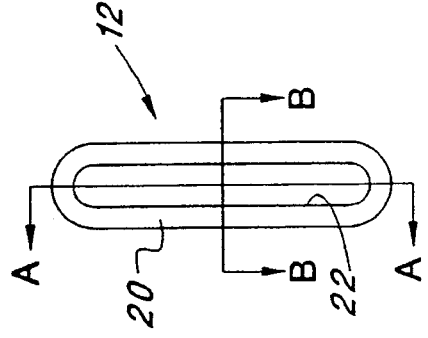
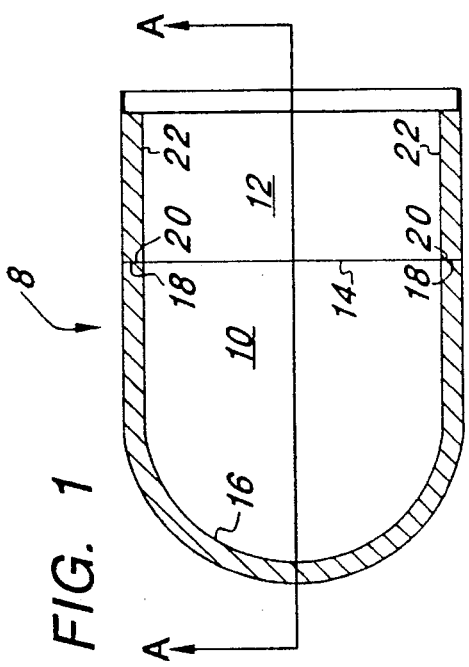
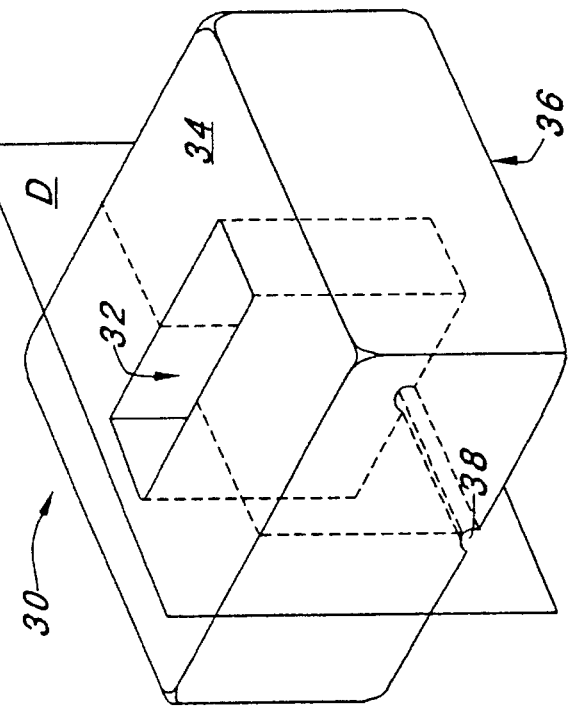
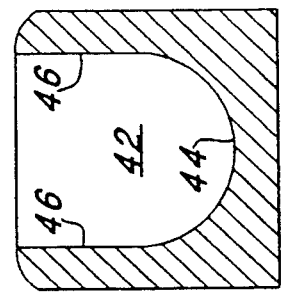
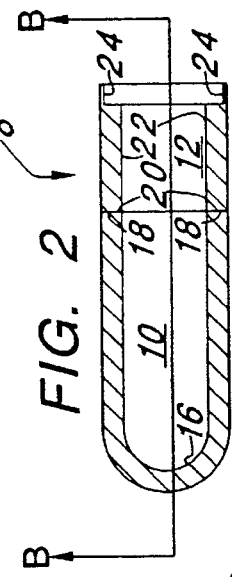
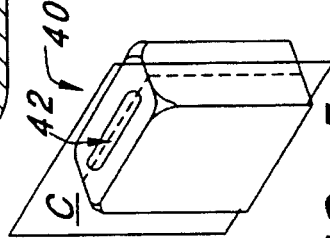

BRAZELESS CERAMIC-TO-METAL BOND FOR USE IN IMPLANTABLE DEVICES

BACKGROUND OF THE INVENTION

The present invention relates to bonding of materials, and more particularly to brazeless bonding of dissimilar materials. Even more particularly, the present invention relates to brazeless hermetically sealed bonding of ceramic to metal for use in implantable devices.

stimulators that are to be implanted in living bodies and powered from external informational sources must be housed in packages of biocompatible material. Such packages must protect the electronic circuitry within the implanted stimulator from body fluids and ions so that the circuitry can survive for extended periods without any significant changes in performance.

Today, the most commonly used metals for implantable packages are titanium, stainless steel and cobalt-chromium alloys. These metals are biocompatible and corrosion resistant. Normally, the package consists of two parts welded together to insure hermeticity. The electrical components inside the package are connected to stimulating leads by hermetic feedthroughs, which permit the flow of electrical currents through the package while maintaining hermeticity. However, where there is a need to inductively couple an alternating electromagnetic field to an internal pickup coil, the metal package becomes a hinderance. Specifically, transmission of power is substantially reduced by eddy currents generated in the metal package due to the alternating electromagnetic field. To solve that problem, receiving coils are often placed outside the metal package, increasing the size and complexity of the of the implanted device.

It is known that the glasses and ceramics are transparent to alternating electromagnetic fields and that receiving antennas can be placed inside a hermetic zone of a ceramic or glass package, creating an overall smaller and simpler implant device and reducing the possibility of antenna failure due to saline leakage. Glasses and ceramics are inert and highly insoluble, which are favorable characteristics for long term implant materials. Unfortunately, however, because glasses and ceramics are inelastic, they are subject to fracture not only from mechanical shock but also from differential thermal expansion if even a moderate temperature gradient exists thereacross. Therefore, welding is not a practical method of sealing glass or ceramic materials. Instead, virtually the entire package and its contents must be raised to the melting temperature of the glass, ceramic or metal braze used to effect a sealing of the glass or ceramic package. Such sealing methods are unsatisfactory.

All known biocompatible glasses and ceramics are characterized by high sealing temperatures that will damage electronic components commonly included in electronic devices implanted in living bodies. Low melting temperature glasses all have the property of being corroded by body fluids. Further, metal or glass frits and solders useful in brazing glasses and ceramics and having melting temperatures below the thermal damage limits of implanted electronic components are either not biocompatible or corrode easily in body solutions. Therefore, packages composed entirely of ceramic and/or glass are not considered practical for such implant applications.

Also, in many ceramic and glass packages, the metal solder used to seal the main body and cap portions thereof forms a closed loop that is very close to coaxial with, or in a plane parallel to, the receiving coil used as the antenna for the electronics housed in the implantable package. Thus configured, the closed metal loop or solder acts as a shunt to the alternating electromagnetic fields impressed upon the package to transmit power and/or data to the implanted electronics. This has resulted in the generation of undesired heat within the package and the reduction of power transfer efficiency.

A packaged combination of one ceramic and two metal members is shown in U.S. Pat. No. 4,991,582, issued to Byers et al. and incorporated herein by reference. The one ceramic member is a ceramic case and one of the metal members is a metal band. The other metal member is a header plate. The ceramic case and the metal band are hermetically sealed together, each being characterized by similar coefficients of linear thermal expansion. The final package closure is effected by soldering the metal band to the ceramic case and the metal header plate to the metal band.

The junction between the ceramic case and metal band includes a bond of flat and smooth non-interlocking geometries. By such a design, forces resulting from unequal expansion or contraction of materials in or near the junction of the ceramic and metal members during temperature changes within and about the package are very inefficiently transferred to the ceramic members. This reduces the risk of residual strain and ultimately of fractures in the ceramic.

Alternatively, where the coefficients of linear thermal expansion of the ceramic case and metal band are similar, i.e., very close, the junction between the ceramic case and metal band may be interlocking to effect a self-jigging of the members during assembly. In such a form, temperature changes will produce corresponding changes in the geometries of the ceramic and metal members and undesired stresses on the junction will be minimized.

More particularly, the ceramic case shown in the '582 patent consists of a hollow flattened ceramic sleeve having a closed end and side walls and an open end for receiving electronic components of an implantable device, which are adversely sensitive to high temperatures such as those components that receive and transmit electromagnetic energy from or to the outside of the package. The coils comprising the antenna are positioned within the ceramic sleeve remote from and in a plane transverse and preferably normal to a flat annular end surface around the open end of the ceramic sleeve where the metal band is bonded. The metal band has a flat annular edge hermetically sealed as by a biocompatible metallic braze or glass solder to the flat annular end surface of the ceramic sleeve. Thus configured, the closed metal loop formed by the metal band and/or metal solder does not act as a shunt to power and/or information conveying alternating electromagnetic fields impressed upon the package and antenna of the present invention.

Finally, the header plate closes the package by means of an hermetic bond to the metal band. The header plate carries a plurality of electrical feedthrough connectors for connecting electrical leads to the electronic components within the package. The metal sleeve is bonded by high temperature welding, such as electron beam or laser welding, to the metal band after the electrical components are mounted in the ceramic sleeve (or case) and adequate heat sinking is applied to insure that there is no heat transfer to any heat sensitive electronic components or ceramic package component during the hermetic sealing operation.

Unfortunately, the package shown in the '582 patent still requires the use of a hermetically sealed weld or solder joint between the ceramic case and the metal band that suffers from one or more the following problems: (a) lack of biocompatability; (b) lack of corrosion resistance; (c) lack of electrolytic compatibility; (d) susceptibility to cracking of the ceramic case; and/or (e) toxicity. Thus, improvements are needed to overcome these problems with hermetically sealed bonds of ceramic to metal in packages for implantable devices.

SUMMARY OF THE INVENTION

The present invention advantageously addresses the needs above as well as other needs by providing an apparatus and method for forming a brazeless hermetically sealed bond.

The invention may be characterized as a method of forming the hermetically sealed bond between materials. The method includes positioning a first structure, made from a first material, against a second structure, made from a second material. A compressive force directed at the second structure is applied to the first structure, and an equal force directed at the first structure in a direction opposite the compressive force is applied to the second structure so that the first and second structures are isodynamically pressed together.

Next, the first and second structures are heated to a diffusion temperature whereat the first material and the second material undergo diffusion, thereby forming a hermetically sealed bond between the first and second materials. In this way, the hermetically sealed bond is formed between the first and second structures.

In one embodiment, the first structure is inserted or slid into a cavity of an inner jig through an open end of the cavity until the first structure seats against a closed end of the cavity. Next, the second structure is placed against a portion of the first structure that is exposed through the open end of the cavity. The second structure may be partially inserted into the cavity through the open end before it seats against the first structure, or the second structure may seat against the first structure at or outside the open end.

An outer jig is placed against a support surface, and then the inner jig is inserted into an open-ended cavity of the outer jig. Outer walls of the inner jig slide against inner walls of the outer jig's open-ended cavity so as to restrict the sliding of the inner jig to be along a single coordinate axis. The support surface lies in a plane substantially normal to the single coordinate axis, with the open end of the inner jig's cavity being oriented toward the plane and the closed end of the inner jig's cavity being oriented away from the plane. The second structure is also oriented toward the plane.

As the inner jig is slid into the outer jig, the second structure seats against the support surface. As a result, the sliding of the inner jig into the outer jig is stopped. The compressive force is applied against the inner jig toward the support surface and along the single coordinate axis. The compressive force is translated to the first structure by the closed end of the inner jig's cavity. The equal force is exerted by the support surface in the direction opposite the compressive force, and is translated to the second structure by the support structure. In this way, a hermetically sealed bond is created between the first structure and the second structure.

The invention may also be characterized as an apparatus for forming a hermetically sealed bond between materials. The apparatus includes: an inner jig; an outer jig; a support surface; compressing means; and heating means.

The inner jig has outer walls, and a cavity. The cavity has an open end formed so as to receive a first structure, and has a closed end against which the first structure can be seated. The outer jig has an open-ended cavity having inner walls that slidably engage the outer walls of the inner jig. When the outer walls of the inner jig are slidably engaged against the inner walls of the outer jig, movement of the inner jig is restricted to be along a single coordinate axis.

The support surface has a substantially planar surface against which the outer jig is supported, and that is substantially normal to the single coordinate axis. Before the inner jig is slid into the outer jig, a second structure is interposed between the first structure and the support surface. The second structure may be inserted into the open end of the inner jig's cavity, and seat against the first structure therein, or may seat against the first structure at or outside the open end of the inner jig's cavity. Such will depend on whether the first structure protrudes through the open end of the inner jig's cavity when the first structure seats against the closed end of the inner jig's cavity.

The compression means applies a compressive force applied against the inner jig, which is translated to the first structure by the inner jig. The compressive force is oriented toward the planar surface along the single coordinate axis. The compression means further applies an equal force opposite the compressive force to the support surface. The support surface translates the equal force to the second structure so as to isodynamically compress a bonding junction between the first and second structures.

The heating means heats the first and second structures to a diffusion temperature. At the diffusion temperature, a first material in the first structure and a second material in the second structure undergo diffusion. As a result, a hermetically sealed bond is formed between the first and second structures.

It is therefore a feature of the invention to provide a method and apparatus for forming a hermetically-sealed bond between a first structure and a second structure.

It is another feature of the invention to form such hermetically-sealed bond without the need for soldering.

It is a further feature of the invention to form such hermetically-sealed bond while maintaining biocompatability, corrosion resistance and electrolytic compatibility, and eliminating toxicity.

It is an additional feature of the invention to form such bond while minimizing the risk of cracking in the first and/or second structures.

BRIEF DESCRIPTION OF THE DRAWINGS

The above and other aspects, features and advantages of the present invention will be more apparent from the following more particular description thereof, presented in conjunction with the following drawings wherein:

FIG. 1 is a cross-sectional view of a case and a band having been bonded together in accordance with one embodiment of the invention taken along a first sectional plane;

FIG. 2 is another cross-sectional view of the case and the band having been bonded together as in FIG. 1 taken along a second sectional plane that intersects line A—A of FIG. 1 and that is normal to the first sectional plane, which intersects line B—B in FIG. 2;

FIG. 3 is an end view of the band of FIGS. 1 and 2 showing a flat annular surface to which a similar flat annular surface of the case is bonded;

FIG. 4 is a perspective view of an outer jig that can be used in bonding together the case and band of FIGS. 1, 2 and 3;

FIG. 5 is a perspective view of an inner jig that can be used in conjunction with the outer jig of FIG. 4 when bonding together the case and band of FIGS. 1, 2 and 3;

FIG. 6 is a cross-sectional view of the inner jig of FIG. 5 taken along plane C of FIG. 5;

FIG. 7 is a side view of the inner jig of FIG. 5 shown perpendicular to plane C of FIG. 5;

Corresponding reference characters indicate corresponding components throughout the several views of the drawings.

DETAILED DESCRIPTION OF THE INVENTION

Figure 8:
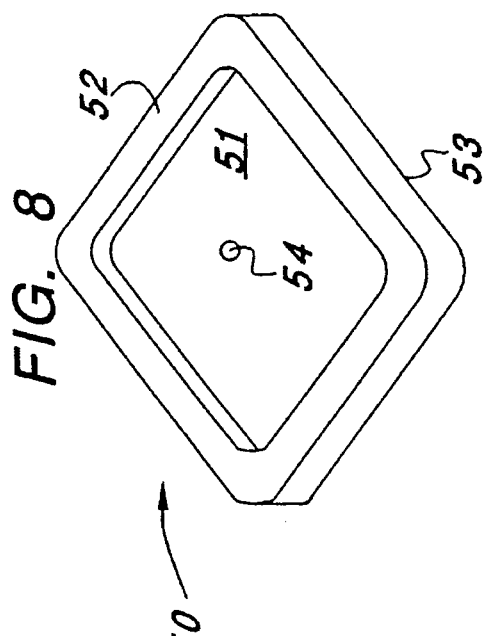
FIG. 8 is a perspective view of a support surface that is utilized in conjunction with the outer jig of FIG. 4 and the inner jig of FIGS. 5, 6 and 7 in bonding together the case and band of FIGS. 1, 2 and 3.

The following description of the presently contemplated best mode of practicing the invention is not to be taken in a limiting sense, but is made merely for the purpose of describing the general principles of the invention. The scope of the invention should be determined with reference to the claims.

Referring first to FIG. 1, a cross-sectional view is shown of a case 10 and a band 12 (or case/band assembly 8) having been bonded together at a bonding site 14. Similarly, in reference to FIG. 2, a cross-sectional view is shown of the case 10 (or first structure) and the band 12 (or second structure) having been bonded together at the bonding site 14. The view shown in FIG. 1 is taken along line B—B shown in FIG. 2, and the view shown in FIG. 2 is taken along line A—A shown in FIG. 1. In both FIGS. 1 and 2, the case 10 is shown as having a "D" shaped cross section. Such cross section facilitates implantation and accommodates any electronic components that are to be housed within the case/band assembly 8, as well as one or more coils that can be housed within the case/band assembly 8.

The case 10 is preferably made from a body-safe ceramic, e.g., Alumina ($AlO_2$) or Zirconium Oxide ($ZO_2$), and is open at its straight end, i.e., the straight end of the "D" shape while its curved end and side walls are closed. Walls 16 of the case 10 terminate around the open end forming a first annular surface 18.

Referring next to FIG. 3, an end view is shown of the band 12 showing a second flat annular surface 20 (also shown in FIGS. 1 and 2) to which the first flat annular surface 18 of the case 10 is ultimately bonded. The band 12 is preferably made from a body-safe metal, e.g., an alloy of Titanium-45 Niobium (i.e., 55% Ti and 45% Nb), available from Teledyne Wha Chang of Albany, N.Y., or numerous other sources, or any other metal or alloy that readily forms an instant oxide when heated, i.e., that readily oxidizes when heated in an oxygen-containing atmosphere. Note that both the alumina and the Titanium-45 Niobium have thermal coefficients of expansion (TCEs) of between 8 and 9 $mm^3$/°C. This minimizes the risk of cracking when the case 10 and band 12 are bonded together at high temperature and then cooled. The band 12 has two open ends. Side walls 22 of the band case 12 terminate at each of the open ends, forming the second flat annular surface 20 at one of the ends, and having, e.g., a flanged edge 24 at another of the ends, which can be for receiving a header plate (not shown). See, e.g., U.S. Pat. No. 4,991,582, previously incorporated herein by reference.

Figure 9:
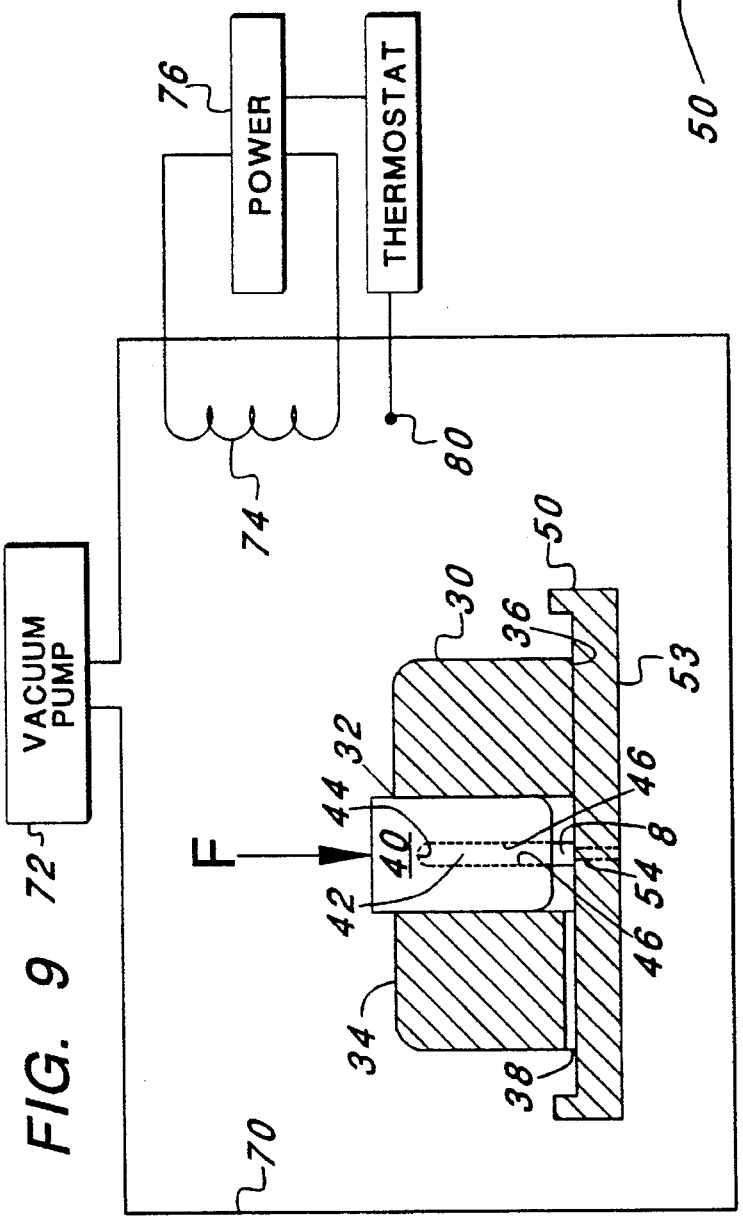
FIG. 9 is a partial cross sectional view of the outer jig of FIG. 4, taken along plane D of FIG. 4, and the inner jig of FIGS. 5, 6 and 7.

Referring next to FIG. 4, a perspective view is shown of an outer jig 30 that is used in bonding the case 10 and band 12 together. The outer jig 30 has generally a rectangular three dimensional shape with a rectangular cavity 32 passing therethrough. The upper surface 34 is identical to the lower surface 36 except for a channel 38 in the lower surface 36 that passes from the center of one of the outer side edges of the outer jig 30 to the center of one of the inner side edges of the cavity 32. The channel 38 is also illustrated in FIG. 9 and is explained more fully below.

The dimensions of the outer jig 30 are dictated by the size and shape of the case 10 and band 12 that are bonded together. For the case 10 and band 12, shown in the figures, the outer jig 30 is preferably made from ALUMINA, available from ICI Advanced Ceramics, and has the following outer dimensions: 8.97×7.06×3.81 cm. The dimensions of the cavity 32 are preferably: 3.89×1.98×3.81 cm, and the channel preferably has a cross sectional area of 7.70 $cm^2$. The outer jig 30 preferably has beveled or rounded edges to improve its appearance and to facilitate its handling.

Referring next to FIG. 5, a perspective view is shown of an inner jig 40 that is used in conjunction with the outer jig 30 in bonding together the case 10 and band 12. Like the outer jig 30, the inner jig 40 has generally a rectangular three dimensional shape. The inner jig 40 has a cavity 42 opening on one of its sides that is formed so as to receive the case 10. When the case 10 is inserted into the cavity 42 it to is held with all of the interior walls of the cavity 42 touching all of the exterior walls of the case 10.

For the preferred embodiment shown in the figures, the inner jig 40 is preferably made from ALUMINA, available from ICI Advanced Ceramics, and has the following outer dimensions: 3.81×1.90×3.81 cm so that the inner jig 40 can be slid into the cavity 32 of the outer jig 30. The inner jig 40 preferably has beveled or rounded edges to improve its appearance and handling.

In practice, the case 10 is slid into the inner jig's cavity 42 until it becomes seated against a closed end 44 (FIG. 6) and side walls 46 (FIG. 6) of the cavity 2. After the case 10 is slid into the cavity 42, the band 12 is slid into the cavity 42 until the second flat annular surface 20 (FIGS. 1 and 2) seats against the first flat annular surface 18 (FIGS. 1 and 2) of the case 10. The band 12 protrudes from the cavity 42 when it is seated against the case 10, as shown in FIG. 9 below.

Referring to FIG. 6, a cross sectional view of the inner jig is shown taken along plane C of FIG. 5. As viewed in FIG. 6, the cavity 42 in the inner jig 40 is substantially "D" shaped so as to accommodate the "D"-shaped case/band assembly 8 of FIG. 1 (or case 10 and band 12, before they are bonded together).

Referring next to FIG. 7, a side view is shown perpendicular to plane C of FIG. 5 of the inner jig. The inner jig 40 is shown, and the cavity 42 is shown with dashed lines. The cavity 42 also has a "D" shaped cross section as viewed in FIG. 7, which accommodates the "D"-shaped cross section of the case/band assembly 8 as viewed in FIG. 2 (or case 10 and band 12, before they are bonded together).

Referring next to FIG. 8, a perspective view is shown of a support surface 50 that is utilized in conjunction with the outer jig 30 and the inner jig 40 in bonding the case 10 and band 12. The support surface 50 has a lip 52 at the periphery of an upper side 51 of the support surface 50. The lip 52 is used to keep powdered titanium oxide on the support surface

50. (Use of the powdered titanium oxide powder is described below.) A lower side 53 of the support surface is supported against, e.g., an alumina plate, which in turn rests against a rack or grill within a vacuum oven, described below.

The support surface 50 has a vent hole 54 near its center that allows gasses to readily enter and exit the case/band assembly 8 when the other open end of the band 12, i.e., not the end that is against the open end of the case 10, is aligned over the vent hole 54.

Referring to FIG. 9, a partial cross sectional view is shown of the outer jig 30, the inner jig 40, the support surface 50, and the case/bend assembly 8. The lower surface 36 of the outer jig 30 is held by gravity against the upper side 51 of the support surface 50 with the upper jig's channel 38 having a central longitudinal axis within the plane of the paper in FIG. 9, and shown to the left of the cavity 32 of the outer jig 30.

The case 10 is inserted into the inner jig's cavity 42 until it seats against the closed end 44 and sides 46 of the inner jig 40. Next, the band 12 is inserted into the cavity 42 until it seats against the case 10 and the sides 46 of the cavity 40. The band 12 protrudes from the cavity when seated against the case 10 and sides 46.

Before inserting the case 10 and band 12 into the cavity 42, however, the interior surface of the cavity 42, as well as the upper side 51 of the support surface 50, is coated with powdered titanium oxide ($TO_2$) to prevent the case 10 and band 12 from bonding to the inner jig 40 and support surface 50.

The inner jig 40, with the band 12 protruding therefrom, is inserted cavity-first into the outer jig 30 through the open end of the outer jig's cavity 32 at the upper surface 34 of the outer jig 30. The inner jig 40 is inserted into the outer jig's cavity 32 until the band 12 protruding from the inner jig 30 seats against the support surface. The inner jig 30 does not come into contact with the support surface 50.

While the inner jig 30 is sliding into the outer jig's cavity 32, the inner jig's movement is restricted to movement along a single coordinate axis, which is preferably normal to the support surface 34, i.e., the plane defining the upper side 51 of the support surface 50.

The other open end of the band, i.e., the open end of the band 12 that is not seated against the case 10, is centered over the vent hole 54, and a chamber formed by the space within the outer jig's cavity 32, below the inner jig 40, above the support surface 50 and outside the band 12, is vented by the channel 38 in the outer jig 30.

The support surface 50, outer jig 30, inner jig 40, case 10 and band 12 are placed onto, e.g., a grate (not shown) in a vacuum oven 70, and a compressive force F is applied along the single coordinate axis to the inner jig 40 in a downward direction, as depicted in FIG. 9 by the downward pointing arrow. This force may be applied by placing weights subject to gravity on top of the inner jig 40. The weights can be secured by wrapping stainless steel bands over the top of the weights and securing them under the support surface 50. Preferably, four or more bands having a width of 1.27 cm and a thickness of 0.025 cm are used. The compressive force applied should be from between 950 $N/m^2$ to 1500 $N/m^2$.

The compressive force F is translated to the case 10 by the inner jig 40. Note also that an equal force is applied by the support surface 50, to the band 12 along the single coordinate axis opposite the direction of the compressive force F. The compressive force F and the opposing equal force isodynamically press the case 10 and band 12 together at the sight where the second flat annular surface 20 of the band 12 is seated against the first flat annular surface 18 of the case 10.

Next, a sealed chamber of the vacuum oven 70 is evacuated to at least $10^{-5}$, preferably $10^{-6}$, atmospheres using a vacuum pump 72. The vacuum oven 70 is then heated by energizing a heating coil 74 using a power supply 76. The temperature in the vacuum oven is heated at the rate of approximately 5° C./minute until it reaches a temperature of at least 1000° C., preferably to between 1000° C. and 1100° C. This temperature is maintained for about 2 hours, i.e., 120 minutes, by a thermostat 78 that is coupled to the power supply 76. The thermostat 78 uses a temperature probe 80 to monitor the temperature within the vacuum oven 70. After the 2 hours, the vacuum oven 70 is cooled at a rate of approximately 1° C./minute, which generally takes about 17 hours, e.g., 1000 minutes, at ambient temperature. Preferably, no forced cooling is performed, i.e., no cold gas spray, or other exposure to a cold environment. Note that during the cooling of the vacuum oven 70, the heating coil 74 will generally remain energized, at least partially, in order to assure that the desired slow rate of cooling is achieved, i.e., 1° C./minute.

During the time the case 10 and band 12 are heated and pressed together, titanium atoms from the band diffuse into the alumina of the case 10. This is caused by an attraction of the titanium atoms to oxygen atoms that are loosely held by the alumina at the above-mentioned temperatures. When the case 10 and band 12 are cooled, the titanium atoms share the oxygen atoms with the alumina.

In this way, a hermetically sealed bond is formed between the case 10 and band 12, so that the case 10 and band 12 can be safely utilized to house an implantable electronic device. Advantageously, the bonding does not degrade or crack the metal or ceramic, and they each maintain their hermeticity.

A header plate (not shown) is used to seal the other end of the band after electronic circuits, and, e.g., inductive pickup coils, are inserted into the case/band assembly 8. The header plate is bonded to the band by, e.g., welding, as is described in U.S. Pat. No. 4,991,582, previously incorporated herein by reference. Note that because the electronic circuits are not inserted into the case/band assembly 8 until after the cooling, and because the header plate can be sealed to the other open end of the band 12 without the need for heating the entire case/band assembly 8 to high temperatures, the electronics are much less prone to heat damage than with many heretofore utilized techniques for bonding the ceramic case 10 to the metal band 12.

While the invention herein disclosed has been described by means of specific embodiments and applications thereof, numerous modifications and variations could be made thereto by those skilled in the art without departing from the scope of the invention set forth in the claims.

What is claimed is:

1. A method of forming a hermetically sealed bond between materials including:

positioning a first structure against a second structure, the first structure including a first material and the second structure including a second material;

applying a compressive force to the first structure, the compressive force being directed at the second structure;

applying an equal force to the second structure, the equal force being directed at the first structure and being in a direction opposite the compressive force;

heating the first and second structures to a diffusion temperature whereat the first material and the second material undergo diffusion so as to cause a hermetically sealed bond between the first and second materials;

whereby the hermetically sealed bond is formed between the first and second structures.

2. The method of claim 1 wherein said positioning includes positioning said first structure against said second structure, said first structure including said first material, wherein said first material includes a ceramic, and said second structure including said second material, wherein said second material includes a metal.

3. The method of claim 2 wherein said positioning includes positioning said first structure against said second structure, said first structure including said first material, wherein said first material includes alumina, and said second structure including said second material, wherein said second material includes titanium.

4. The method of claim 2 wherein said positioning includes positioning said first structure against said second structure, said first structure including said first material, and said second structure including said second material, wherein a thermal coefficient of expansion of said first material differs from a thermal coefficient of expansion of said second material by no more than 2 mm$^3$/° C.

5. The method of claim 1 wherein:

said positioning includes:

inserting said first structure into a cavity in an inner jig;

placing an outer jig against a support surface; and sliding the inner jig into the outer jig, wherein outer walls of the inner jig slide against inner walls of the outer jig and restrict the sliding of the inner jig to be along a single coordinate axis, the support surface lying in a plane substantially normal to the single coordinate axis, the cavity of the inner jig having an open end into which said first structure is inserted, the open end being oriented toward the plane, the inner jig having a closed end against which said first structure is seated, the closed end being oriented away from the plane, said second structure positioned against the first structure at an end of said first structure that is oriented away from the closed end; and said applying of said compressive force includes:

engaging the second structure against the support surface so as to stop the sliding of the inner jig into the outer jig; and applying said compressive force against the inner jig toward the support surface and along the single coordinate axis, said compressive force being translated to said first structure by said inner jig, said equal force being exerted by said support surface in said direction opposite said compressive force, said equal force being translated to said second structure by said support structure.

6. The method of claim 5 wherein said heating includes:

enclosing said first and second structures in a sealed chamber; and evacuating the sealed chamber to at least 10$^{-5}$ atmospheres.

7. The method of claim 6 wherein said heating includes heating said first and second structures to at least 1000° C.

8. The method of claim 7 wherein said heating includes heating said first and second structures for at least 120 minutes.

9. The method of claim 5 wherein said applying of said compressive force includes applying said compressive force, wherein said compressive force has a magnitude of at least 950 N/m$^2$.

10. A method of forming a hermetically sealed bond between a first structure and a second structure, the method including:

compressing isodynamically a first structure against second structure, so as to isodynamically press the first structure and the second structure together at a bonding junction; and heating the first and second structures to a diffusion temperature, the first structure including a first material and the second structure including a second material, the first material and the second material undergoing diffusion in response to the heating, and the diffusion causing a hermetically sealed bond between the first and second materials;

whereby a hermetically sealed bond is formed between the first structure and the second structures.

11. The method of claim 10 wherein said compressing includes applying a force of at least 950 N/m$^2$.

12. The method of claim 10 wherein said heating includes heating said first and second structures to a temperature of at least 1000° C.

13. The method of claim 12 wherein said heating includes heating at the rate of 4° C./minute.

14. The method of claim 12 including:

cooling the first and second structures at the rate of 1° C./minute.

15. The method of claim 10 wherein said compressing includes:

sliding said first structure into a cavity of an inner jig;

seating, in response to the sliding of said first structure, said first structure against a closed end of the cavity of the inner jig;

placing said second structure against an end of said first structure that is exposed through an open end of the cavity of the inner jig;

sliding the inner jig into an opening of the outer jig, the opening being open at one end thereof and having a support surface at another end thereof, the sliding being from the one end of the opening toward the other end of the opening along a single coordinate axis; and seating, in response to the sliding of the inner jig, the second structure against the support surface.

* * * * *